United States Patent [19]

Loev et al.

[11] 4,258,042
[45] Mar. 24, 1981

[54] ANTIHYPERTENSIVE PYRIDINES AND COMPOSITIONS

[75] Inventors: Bernard Loev, Scarsdale, N.Y.; James R. Shroff, Riverside, Conn.

[73] Assignee: USV Pharmaceutical Corporation, Tuckahoe, N.Y.

[21] Appl. No.: 139,367

[22] Filed: Apr. 11, 1980

[51] Int. Cl.³ .................. A61K 31/535; C07D 295/14
[52] U.S. Cl. ........................... 424/248.5; 424/248.51; 424/248.52; 424/248.54; 424/248.55; 544/122; 544/128; 544/131
[58] Field of Search ...................... 544/122, 128, 131; 424/248.51, 248.52, 248.5, 248.54, 248.55

[56] References Cited
FOREIGN PATENT DOCUMENTS
51-70767  6/1976  Japan .

Primary Examiner—John D. Randolph
Assistant Examiner—R. W. Ramsuer
Attorney, Agent, or Firm—Ernest B. Lipscomb, III

[57] ABSTRACT

Antihypertensive compounds of the formula

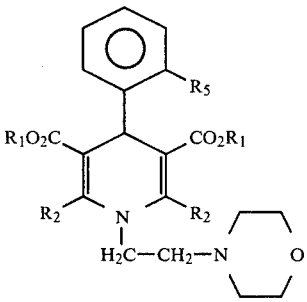

wherein $R_5$ is H, alkyl, aryl, halo, lower alkoxy, nitro amino, alkylmercapto, cyano, carboxy, carbalkoxy, sulfamyl, trifluoromethyl, hydroxy, acyloxy, methanesulfonyl, alkylamino or acylamino; and each $R_1$ and $R_2$ is alkyl; wherein the alkyl, alkoxy and aryl groups contain up to 10 carbon atoms and non-toxic, pharmaceutically-acceptable acid addition salts thereof.

11 Claims, No Drawings

ANTIHYPERTENSIVE PYRIDINES AND COMPOSITIONS

This invention relates to new anti-hypertensive agents and more particularly to certain new substituted 1,4-dihydropyridines possessing useful anti-hypertensive activity.

Substituted 1,4-dihydropyridines are known and have been described in the literature as vasodilating agents. 1,4-dihydropyridines having vasodilating activity are characterized by the presence of alkyl substituents in the 2 and 6 positions of the pyridine ring and carbalkoxy groups in the 3,5-positions usually with a substituent, most commonly phenyl or substituted phenyl, in the 4-position. To increase the water-solubility of these compounds, M. Iwanami, et al. [Chem. Pharm. Bull. 27 (6) 1426–1440 (1979)] described the effect of N-substitution of the pyridine ring nitrogen with, inter alia, aminoalkylene groups such as pyrollidinoethyl and dimethylaminoethyl. Thus, water-solubility determinations with compounds such as diethyl 1,4-dihydro-4-(3-nitrophenyl)- 2,6-dimethyl-1-(2-pyrrolidinoethyl)-aminoethyl) compound were determined as was the potency thereof as vasodilators but these compounds were determined to be of lower potency than known compounds such as the corresponding 1-ethoxymethyl compound.

Japanese Pat. No. 70767/76 describes as anti-hypertensive and vasodilating agents 1,4-dihydropyridines of the formula

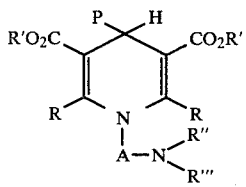

in which R is alkyl; P is substituted (mono or di-) phenyl, pyridyl, furyl, or thienyl in which the substituents are H, halogen, —CN, —NO$_2$, —NH$_2$, —N(CH$_3$)$_2$, carboxyl, methoxy, ethoxy, butoxy, solfonyl, methylsulfonyl or acetyl; R' is alkyl, aralkyl, methyl, ethyl, isopropyl, t-butyl, ethoxyethyl, benzyl, phenethyl, or 4-methoxybenzyl; A is alkylene; and R" and R''' are each alkyl and, when taken together with the N to which they are attached form a pyrollidine ring.

U.S. Pat. No. 3,441,648 describes anti-hypotensive 1,4-dihydropyridines of the formula

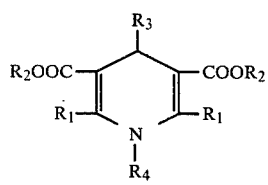

in which R$_1$ and R$_2$ are lower alkyl having 1–6 carbon atoms R$_3$ is phenyl, halophenyl, dihalophenyl, lower alkylphenyl, di-lower alkylphenyl, tri-lower alkylphenyl, lower alkoxyphenyl, di-lower alkoxyphenyl, tri-lower alkoxyphenyl, trifluoromethylphenyl, benzyl, styryl, furyl, thienyl, pyridyl or pyrrolidyl, said lower alkyl and lower alkoxy groups having 1 to 4 carbon atoms and R$_4$ is hydrogen or lower alkyl having 1–6 carbon atoms.

The new compounds of the present invention are N-morpholinoalkyl dihydropyridines of the formula:

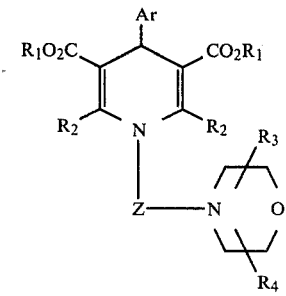

FORMULA I wherein Ar is heteroaryl, cycloalkyl having from 3 to 7 carbon atoms, naphthyl, indanyl, indenyl, tetrahydronaphthyl or a radical of formula

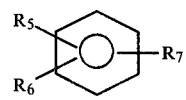

wherein each of R$_5$, R$_6$ and R$_7$ is independently H, alkyl, aryl, halo, lower alkoxy, nitro, amino, alkylmercapto, cyano, carboxy, carbalkoxy, sulfamyl, trifluoromethyl, hydroxy, acyloxy, methanesulfonyl, alkylamino or acylamino; and R$_5$ and R$_6$ when taken together form a methylenedioxy; Z is alkylene containing 1 to about 5 carbon atoms in the principal chain; and each R$_1$ is independently hydrogen, alkyl, or alkoxyalkyl, with the proviso that only one R$_1$ may be hydrogen; R$_2$ is lower alkyl; R$_3$ and R$_4$ are independently hydrogen or lower alkyl; and non-toxic, pharmaceutically acceptable acid addition salts thereof. The total number of carbon atoms in each of the alkyl, acyl, and alkoxy groups can range up to about 10, and preferably contain up to 6 carbon atoms. The substituent "Z" contains up to about 5 carbons in the principal chain, i.e. the straight chain of carbons between the terminal valences, but can be branched in that methyl and ethyl substituents can be present on the principal chain. Thus, the alkylene chain Z can contain a total number of carbon atoms greater than 5, preferably no more than about 8.

Heteroaryl as employed herein refers to any heterocyclic structure in which at least one of O, S and N are present as the hetero atoms. These include thiophene, furan, pyridine, thiazole, pyrimidine, pyrrole, benzofuran, quinoline, benzothiophene and substituted heterocycles.

The preferred compounds are those in which the hydrocarbyl radicals contain up to about 7 carbon atoms when aliphatic and up to about 10 carbon atoms when aromatic, e.g., phenyl, tolyl and naphthyl.

The particularly preferred compounds of the invention are those in which Z is

—CH$_2$CH$_2$— and Ar is a trifluoromethylphenyl group, especially 2-trifluoromethylphenyl.

The new compounds of the invention can be prepared by art-recognized procedures from known starting compounds as described, for example, in the literature hereinbefore described. The following procedure constitutes a particularly convenient preparative method:

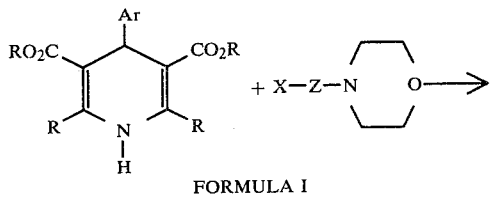

FORMULA I

The reaction can be carried out in a solvent in the presence of sodium hydride, or any alkali metal hydride or alkoxide as is commonly employed in condensation reactions. The reaction is effected in two steps, the first metallation with the alkali metal compound, and the second, condensation with the halide, "X", containing compound, which is usually chloride. The hydrides are convenient since the progress of the metallation reaction can be followed by observing the evolution of hydrogen gas. The metallation step is normally carried out at room temperature. The reaction mixture thereafter is heated at elevated temperature, e.g. at steam bath temperature at or about 100° C. depending on the boiling point of the selected solvent, and the halide compound is then added, usually in controlled amounts in dropwise fashion and, after addition is completed, the reaction mixture is digested by heating at the elevated temperature.

The product is then obtained in the usual fashion, as by cooling to cause precipitation or evaporation of the solvent to obtain the product as a residue.

The new compounds of the invention can also be prepared by allowing an N-aminoalkylmorpholine to condense with an aryl aldehyde and an alkyl acetotate as shown in Example 2.

Employing this procedure, a variety of new N-morpholinoalkyl 1,4-dihydropyridines of the following formula can be prepared:

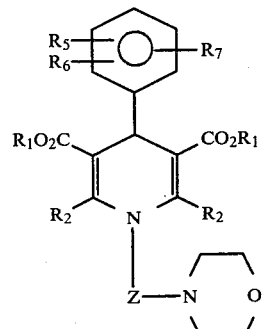

| Z | $R_1$ | $R_2$ | $R_5$ | $R_6$ | $R_7$ |
|---|---|---|---|---|---|
| $CHCH_3$ | $CH_3$ | $C_2H_5$ | H | H | H |
| $CHCH_3$ | $CH_3$ | $C_2H_5$ | H | $CH_3$ | H |
| $CH_2CH_2$ | $CH_3$ | $C_2H_5$ | H | H | H |
| $CH(CH_3)CH_2$ | $C_2H_5$ | $C_2H_5$ | H | H | Cl |
| $CH_2CH_2$ | $CH_3$ | $i-C_3H_7$ | H | CN | H |
| $CH_2CH_2$ | $CH_3$ | $C_2H_5$ | H | H | $NO_2$ |
| $CH_2CH_2$ | $CH_3$ | $C_2H_5$ | H | OH | H |
| $CH_2CH_2$ | $C_3H_7$ | $CH_3$ | H | H | $CF_3$ |
| $CH(CH_3)$ | $C_4H_9$ | $C_2H_5$ | H | $OCH_3$ | H |
| $(CH_2)_3$ | $C_6H_{13}$ | | H | COOH | H |
| $CH_2CH_2$ | $i-C_4H_9$ | $CH_3$ | $OCH_3$ | H | H |
| $CH_2CH_2$ | $CH_3$ | $C_2H_5$ | H | $OCH_3$ | $OCH_3$ |
| $(CH_2)_5$ | $CH_3$ | $C_2H_5$ | H | $CH_3$ | $CH_3$ |
| $CH_2CH_2$ | $CH_3$ | $C_2H_5$ | H | H | $CH_2C_6H_5$ |
| $CH_2CH_2$ | $CH_3$ | $C_2H_5$ | H | H | $C(CH_3)_3$ |
| $CH(CH_3)CH_2$ | $CH_3$ | $C_2H_5$ | H | H | $C_6H_5$ |
| $CH_2CH_2$ | $CH_3$ | $C_2H_5$ | H | H | H |
| $CH_2CH_2$ | $CH_3$ | $C_2H_5$ | Cl | Cl | Cl |
| $CH_2CH_2$ | $CH_3$ | $C_2H_5$ | Cl | H | Cl |
| $CH_2CH_2$ | $CH_3$ | $C_2H_5$ | Cl | H | Cl |
| $CH_2CH_2$ | $CH_3$ | $C_2H_5$ | $OCH_3$ | H | $CH_2=CH-CH_2$ |
| $CH_2CH_2$ | $CH_3$ | $C_2H_5$ | H | H | H |
| $CH_2CH_2$ | $CH_3$ | $C_2H_5$ | H | $CH_3$ | H |
| $CH_2CH_2$ | $CH_3$ | $C_2H_5$ | H | H | H |
| $CH_2CH_2$ | $CH_3$ | $C_2H_5$ | H | $CH_3$ | H |
| $CH_2CH_2$ | $CH_3$ | $C_2H_5$ | H | $CH_3$ | $CH_3$ |
| $CH_2CH_2$ | $CH_3$ | $C_2H_5$ | H | H | H |
| $CH_2CH_2$ | $CH_3$ | $C_2H_5$ | H | H | H |
| $CH_2CH_2$ | $CH_3$ | $C_2H_5$ | H | $CH_3$ | H |
| $CH_2CH_2$ | $CH_3$ | $C_2H_5$ | H | H | Cl |
| $CH_2CH_2$ | $CH_3$ | $C_2H_5$ | H | CN | H |
| $CH_2CH_2$ | $CH_3$ | $C_2H_5$ | $NO_2$ | H | H |
| $CH_2CH_2$ | $CH_3$ | $C_2H_5$ | H | OH | H |
| $CH_2CH_2$ | $CH_3$ | $C_2H_5$ | H | $CF_3$ | H |
| $CH_2CH_2$ | $CH_3$ | $C_2H_5$ | H | $OCH_3$ | H |
| $CH_2CH_2$ | $CH_3$ | $C_2H_5$ | H | COOH | H |
| $CH_2CH_2$ | $CH_3$ | $C_2H_5$ | $OCH_3$ | H | H |
| $CH_2CH_2$ | $CH_3$ | $C_2H_5$ | H | $OCH_3$ | $OCH_3$ |
| $CH_2CH_2$ | $CH_3$ | $C_2H_5$ | H | H | $OCH_3$ |
| $CH_2CH_2$ | $CH_3$ | $C_2H_5$ | $OCH_3$ | H | $CH_2=CH-CH_2-$ |
| $CH_2CH_2$ | $CH_3$ | $C_2H_5$ | H | H | $COOCH_3$ |
| $CH_2CH_2$ | $CH_3$ | $C_2H_5$ | $OCH_3$ | H | $COOCH_3$ |
| $CH_2CH_2$ | $CH_3$ | $C_2H_5$ | H | H | $-(CH_2)_4-$ |

| Z | $R_1$ | $R_2$ | $R_5$ | $R_6$ | $R_7$ |
|---|---|---|---|---|---|
| -continued | | | | | |
| $CH_2CH_2$ | $CH_3$ | $C_2H_5$ | H | H | $NH_2$ |

The compounds of this invention are characterized by high anti-hypertensive activity with little, if any, adverse side effects. For example, toxicity determinations in mice gave an $LD_0$ value of 320 mg./kg. (intraperitoneal) for diethyl 1,4-dihydro-4-(2-trifluoromethylphenyl)-2,6-dimethyl-1-(2-morpholinoethyl)-3,5-pyridine dicarboxylate whereas the corresponding 1-(2-pyrrolinoethyl) compound showed $LD_{50}$=74 mg./kg. (intraperitoneal). The former compound showed no tachycardia in mice at 30 mg./kg. (per os) whereas the latter caused tachycardia at 1 mg./kg. (intraperitoneal).

The present new heterocyclic compounds are therapeutically useful as such or can be employed in the form of salts in view of their basic nature. Thus, these compounds form salts with a wide variety of acids, inorganic and organic, including nontoxic, pharmaceutically-acceptable acids. The salts with pharmaeceutically-acceptable acids are, of course, useful in the preparation of formulations where water solubility is desired. The salts with pharmaceutically-unacceptable acids are particularly useful in the isolation and purification of the present new compounds. Therefore, all acid salts of the present new compounds are contemplated by the present invention.

The pharmaceutically-acceptable acid addition salts are of particular value in therapy. These include salts of mineral acids such as hydrochloric, hydriodic, hydrobromic, phosphoric, metaphosphoric, nitric and sulfuric acids, as well as salts of organic acids such as tartaric, acetic, citric, malic, benzoic, mandelic, glycollic, gluconic, succinic, nicotinic, arylsulfonic, e.g. p-toluenesolfonic acids, and the like. The pharmaceutically-unacceptable acid addition salts, while not useful for therapy, are valuable for isolation and purification of the new substances. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the new products.

The compounds of the present invention are less acutely toxic and have less tachycardia than the structurally closest analogs disclosed in the prior art.

As therapeutic agents, the present new heterocyclic compounds are particularly useful as anti-hypertensive agents. The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimun dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other anti-hypertensive agents and the dosage level is of the same order of magnitude as is generally employed with these other therapeutic agents. The therapeutic dosage will generally be from 10 to 750 milligrams per day and higher although it may be administered in several different dosage units. Tablets containing from 10 to 250 mg. of active agent are particularly useful.

The following examples further illustrate the invention.

EXAMPLE 1

Diethyl 1,4-dihydro-4-(2-trifluoromethylphenyl)-2,6-dimethyl-1-(2-morpholinoethyl)-3,5-pyridinedicarboxylate.

To a slurry of sodium hydride (2.6 g g., 55 mmole, 50:50 oil dispersion) in dry, distilled DMF (50 mL) under nitrogen atmosphere was added a solution of diethyl 1,4-dihydro-4-(2-trifluoromethylphenyl)-2,6-dimethyl-3,5-pyridine-dicarboxylate (19.9 g., 50 mmole) in DMF (125 mL). After hydrogen bubbling ceased, the reaction mixture was warmed in a water bath for ½ hour, and a toluene (200 mL) solution of N-(2-chloroethyl)-morpholine (8.1 g., 60 mmole) was added dropwise. The reaction mixture was stirred at 110°–115° for 4 hours.

The reaction mixture was cooled, vacuum filtered, and the filtrate was concentrated in vacuo. The brown paste was taken up in refluxing hexane and allowed to crystallize. Recrystallization from hexane afforded a beige solid (yield: 4.3 g.).

EXAMPLE 2

Diethyl 1,4-dihydro-4-(2-trifluoromethylphenyl)-2,6-dimethyl-1-(2-morpholinoethyl)-3,5-Pyridinedicarboxylate.

In a 100 ml round bottom reaction vessel was placed 17.5 mmol o-trifluoromethylbenzaldehyde (3.0 g) and 5 ml of ethyl aceto-acetate (39 mmol). The mixture was stirred and 20 ml of ethanol were added. To the stirred reaction mixture was added 2.86 g of N-(2-aminoethyl)-morpholine. The reaction mixture was refluxed overnight under a blanket of nitrogen.

The reaction mixture was worked up as follows: The cooled reaction mixture was poured into excess 1 molar citric acid solution and extracted into ethyl acetate. The ethyl acetate phase was separated, cross washed with 1 molar solium bicarbonate solution and finally brine. The ethyl acetate phase was separated, dried with magnesium sulfate and clarified and concentrated to an oil. The oil was chromatographed on silica gel substrate to yield the desired product.

What is claimed is:

1. A compound of the formula:

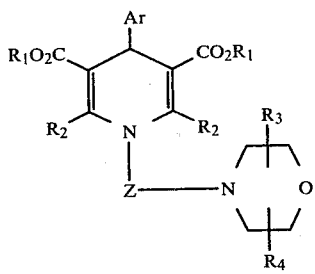

wherein Ar is heteroaryl, cycloalkyl having from 3 to 7 carbon atoms, naphthyl, indanyl, indenyl, tetrahydronaphthyl, or a radical of the formula

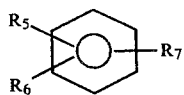

wherein each of $R_5$, $R_6$ and $R_7$ is independently H, alkyl, aryl, halo, lower alkoxy, nitro, amino, alkylmercapto, cyano, carboxy, carbalkoxy, sulfamyl, trifluoromethyl, hydroxy, acyloxy, methanesulfonyl, alkylamino or acylamino; and $R_5$ and $R_6$, when taken together, form a methylenedioxy; Z is alkylene containing 1 to about 5 carbon atoms in the principal chain; each $R_1$ is independently hydrogen, alkyl or alkoxyalkyl, with the proviso that only one $R_1$ may be hydrogen; $R_2$ is lower alkyl; and $R_3$ and $R_4$ are independently hydrogen or alkyl; wherein the alkyl, alkoxy, and acyl groups contain up to 10 carbon atoms, and their non-toxic, pharmaceutically-acceptable acid addition salts.

2. A compound according to claim 1 wherein the alkyl, alkoxy and acyl groups contain up to 6 carbon atoms.

3. The compound according to claim 2 wherein Ar is a monosubstituted phenyl group and Z is —CH$_2$—CH$_2$—.

4. The compound according to claim 1 wherein heteroaryl is thienyl, furyl, thiazolyl, pyridyl or quinolinyl.

5. The compound according to claim 2 wherein Ar is a trifluoromethylphenyl.

6. The compound according to claim 2 wherein Ar is a trifluoromethylphenyl and Z is —CH$_2$—CH$_2$—.

7. Diethyl 1,4-dihydro-4-(2-trifluoromethylphenyl)-2,6-dimethyl-1-(2-morpholinoethyl)-3,5-pyridinedicarboxylate.

8. A non-toxic, pharmaceutically-acceptable acid addition salt of the compound of claim 7.

9. An anti-hypertensive composition comprising an effective amount of a compound according to claim 1 admixed with a pharmaceutically acceptable carrier.

10. An anti-hypertensive compound of the formula

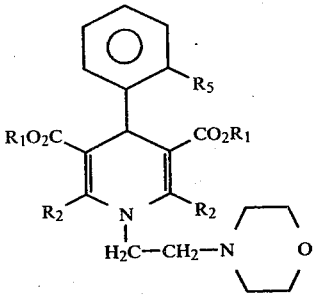

wherein $R_5$ is H, alkyl, aryl, halo, lower alkoxy, nitro, amino, alkylmercapto, cyano, carboxy, carbalkoxy, sulfamyl, trifluoromethyl, hydroxy, acyloxy, methanesulfonyl, alkylamino or acylamino; and each $R_1$ and $R_2$ is alkyl; wherein the alkyl, alkoxy and acyl groups contain up to 10 carbon atoms and non-toxic, pharmaceutically-acceptable acid addition salts thereof.

11. The compound according to claim 10 wherein $R_1$ is ethyl and $R_2$ is methyl, $R_3$ and $R_4$ are hydrogen, and $R_5$ is trifluoromethyl.

* * * * *